United States Patent [19]

Honda et al.

[11] Patent Number: 5,175,308
[45] Date of Patent: Dec. 29, 1992

[54] PREPARATION PROCESS OF INDOLES

[75] Inventors: Tadatoshi Honda, Hiratsuka; Makoto Kotani, Yokohama, both of Japan

[73] Assignee: Mitsui Toatsu Chemicals, Inc., Tokyo, Japan

[21] Appl. No.: 609,641

[22] Filed: Nov. 6, 1990

[30] Foreign Application Priority Data

Nov. 10, 1989 [JP] Japan .................................. 1-291352

[51] Int. Cl.$^5$ .................... C07D 209/30; C07D 209/04
[52] U.S. Cl. ..................................... 548/508; 548/469; 548/489
[58] Field of Search ........................ 548/489, 508, 469

[56] References Cited

U.S. PATENT DOCUMENTS

| 4,476,310 | 10/1984 | Honda et al. | 548/508 |
| 4,831,158 | 5/1989 | Ueno et al. | 548/508 |
| 4,937,353 | 6/1990 | Kudoh et al. | 548/508 |

FOREIGN PATENT DOCUMENTS 654572 2/1986 Switzerland .

Primary Examiner—Joseph Paul Brust
Assistant Examiner—Jacqueline Haley
Attorney, Agent, or Firm—Burns, Doane, Swecker & Mathis

[57] ABSTRACT

A process is provided for the preparation of an indole from aniline or a derivative thereof and a polyhydric alcohol. The reaction is carried out in the presence of a catalyst composed of a carrier having a specific surface area of at least 10 m$^2$/g and silver supported on the carrier. The catalyst also contains as an additional component a specific amount of at least one element selected from Co, Fe and Ni. Deterioration in catalytic performance of the catalyst during the reaction and its regeneration are therefore minimized.

13 Claims, No Drawings

PREPARATION PROCESS OF INDOLES

BACKGROUND OF THE INVENTION

1. Field of the Invention

The present invention relates to a process for the preparation of an indole from aniline or a derivative thereof and a polyhydric alcohol, and more specifically to a preparation process which makes use of a supported silver catalyst.

2. Description of the Related Art

In U.S. Pat. No. 4,476,310, the present inventors have already proposed a process for preparing an indole by reacting aniline or a derivative thereof with 1,2-glycol in the presence of a silver catalyst supported on a carrier whose specific surface area is 10 m²/g or greater. As is also pointed out in U.S. Pat. No. 4,831,158, when the reaction is conducted using such a catalyst, the catalyst is progressively deteriorated as the reaction time goes on. As a result, the conversion of the glycol and the selectivity to indole or the indole derivative are lowered, whereby the yield of indole or the derivative thereof is reduced. The thus deteriorated catalyst can be regenerated by the method disclosed in U.S. Pat. No. 4,831,158, thereby making it possible to resume the reaction. However, the silver catalyst supported on the carrier can retain its activity only for a short time, leading to the need for frequent regeneration. Further, a significant amount of time is required for the regeneration so that the operation rate is impaired. Irreversible deactivation of the catalyst is also unavoidable upon regeneration. There has hence been a strong desire for the development of a catalyst whose catalytic performance undergoes minimized deterioration during both the reaction and the regeneration.

SUMMARY OF THE INVENTION

An object of the invention is therefore to provide a process for preparing an indole from an aniline or a derivative thereof and a polyhydric alcohol in the presence of a catalyst whose catalytic performance undergoes minimized deterioration during both the reaction and the regeneration.

The present inventors have surprisingly found that the object of the invention can be achieved by the use of a silver catalyst, which is supported on a carrier having a specific surface area and contains one or more specific elements in a particular amount, upon preparation of an indole from aniline or a derivative thereof and a polyhydric alcohol, leading to the completion of the invention.

In one aspect of the present invention, there is thus provided a process for preparing an indole by reacting aniline or a derivative thereof with a polyhydric alcohol in the presence of a catalyst composed of a carrier having a specific surface area of at least 10 m²/g and silver supported on the carrier. The catalyst further comprises at least one element selected from Co, Fe and Ni. Said at least one element is contained in a range of from 0.01 to 0.20 on a basis of the atomic ratio to the silver.

The process according to the invention has brought about numerous advantages, including:

(1) The catalyst is substantially free from deterioration for a long time and exhibits considerably-improved retention of the catalytic activity. The conversion of the reactants and the selectivity to the target compound are therefore not lowered to significant extent even after the reaction is continued for a long time.

(2) The catalyst can be easily regenerated after it has been used. Similar to the fresh catalyst, the catalyst thus regenerated does not undergo any substantial deterioration even when employed for a long time in the reaction. The catalyst can therefore be used repeatedly over many hours, thereby making it possible to realize efficient preparation of the indole.

(3) Fewer instances of catalyst regeneration and replacement are required so that the operation rate can be improved. This permits economical preparation of the indole.

DETAILED DESCRIPTION OF THE INVENTION

Aniline and aniline derivatives, which are usable in the present invention, are compounds represented by the following formula (I):

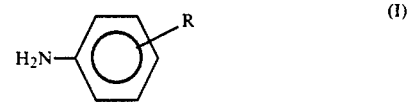

wherein R is a hydrogen or halogen atom or a hydroxyl, alkyl or alkoxy group. Illustrative of such aniline and aniline derivatives include aniline, o-toluidine, m-toluidine, p-toluidine, o-haloanilines, m-haloanilines, p-haloanilines, o-aminophenol, m-aminophenol, p-aminophenol, o-anisidine, m-anisidine and p-anisidine.

Exemplary polyhydric alcohols usable in the invention include ethylene glycol, propylene glycol, 1,2-butanediol, 1,2,4-butanetriol, 2,3-butanediol and diethylene glycol.

The catalyst employed in the invention is a silver catalyst supported on a carrier having a specific surface area of at least 10 m²/g, and additionally contains at least one element selected from Co, Fe and Ni.

Any carrier can be used as long as its specific surface area is 10 m²/g or greater. Numerous carriers are known to have such a specific surface area. It is possible to use, for example, an oxide of at least one element selected from Si, Al, B, Sb, Bi, Sn, Pb, Ga, Ti, Zr, Be, Mg, Y, Zn, Cd and lanthanide elements, or activated carbon.

Among these carriers, particularly preferred are those containing $SiO_2$, notably those containing $SiO_2$—ZnO, $SiO_2$—CdO, $SiO_2$—MgO or $SiO_2$—SrO, and activated carbon.

The amount of silver supported may generally range from 1 wt. % to 50 wt. % although no particular limitation is imposed thereon.

The content of Co, Fe or Ni should be in a range of from 0.01 to 0.20 on a basis of the atomic ratio of the silver supported. Contents smaller than 0.01 are too low to achieve substantial suppression of deterioration. On the other hand, contents greater than 0.20 cannot bring about any significant improvement to the deterioration-suppressing effect. To the contrary, such high contents lead to the inconvenience that the selectivity to the indole will be lowered. It is therefore not preferable to contain Co, Fe or Ni in any proportion outside the above range.

The above element can be incorporated by any method commonly employed in the present field of art, for example, (1) by adding it as one of the raw materials upon preparation of the carrier, (2) by adding it through impregnation, adsorption or mixing after preparation of the carrier, (3) by causing the carrier to support it at the same time as silver is supported, or (4) by adding it through impregnation, adsorption or mixing after silver has been supported. The method (2) is however preferred for good retention of the activity.

For example, water glass and a metal salt (a salt of Zn, Cd, Mg or Sr) are subjected to coprecipitation so that a carrier having a specific surface area of 10 m$^2$/g or greater is obtained.

The carrier described above is immersed for 24 hours in a solution which has been prepared by adding 3-8N aqueous ammonia to an aqueous solution of a Co, Fe or Ni salt at substantially the same equivalent ratio. After the solution is drained, the carrier thus immersed is washed with water and is then calcined at 400°–550° C.

Provided next are an aqueous solution (Solution A) which has been prepared by combining an aqueous solution of a silver salt and 3-8N aqueous ammonia at substantially the same equivalent ratio and a 1–10% aqueous hydrazine solution (Solution B). After the above-calcined carrier is immersed for 24 hours in Solution A, the carrier is dipped for 2–5 hours in Solution B. This procedure is repeated until silver is supported in a predetermined amount. The amount of silver is measured by inductively coupled plasma emission spectrometry (ICP).

The process of the invention is usually conducted in the vapor phase although it can be practiced in any one of vapor phase, liquid phase and mixed vapor-liquid phase.

To practice the process of the invention in the vapor phase, at least one catalyst selected from the above-described catalysts is packed in a reactor tube. After heating the catalyst to a predetermined temperature in a N$_2$ gas stream, N$_2$ gas is changed to H$_2$ gas and the catalyst is reduced for 30 minutes to 3 hours. A mixture of aniline or a derivative thereof and a polyhydric alcohol is then allowed to pass through the reactor tube, whereby they are reacted with each other.

Here, any one of various inert gases can be included as a diluent for the raw materials. Such inert gases can include, for example, nitrogen gas, carbon dioxide gas, steam, and vapors of compounds inert to the reaction. The use of hydrogen gas or a hydrogen-containing gas is preferred to retain the catalytic activity. Steam can suppress decomposition of the polyhydric alcohol on the catalyst, so that the use of steam is preferable for retaining the activity of the catalyst and also for increasing the yield of the target product.

The vapor-phase reaction can be conducted in a fixed-bed, fluidized-bed or moving-bed reactor. No particular limitation is imposed in this respect.

In the catalytic reaction of the invention, the polyhydric alcohol is used in a range of 0.05–5 moles, preferably in a range of 0.1–2 moles per mole of the aniline or the derivative thereof.

After these raw materials are converted into vapor form or as they are, i.e., in liquid form, they are charged directly into the reactor such that they are allowed to have a liquid space velocity of 0.01–5 1/l-catalyst/hr relative to the catalyst. They can also be fed by corresponding constant displacement pumps to an evaporator arranged upstream of the reactor tube, and at the same time water can be fed at a predetermined flow rate to the evaporator.

Non-condensable gas in the reaction product gas flows through a condenser, a gas-liquid separator and a pressure regulator valve and is released into the atmosphere. The condensate is intermittently drawn out of the gas-liquid separator which also serves as a reservoir for the liquid reaction product, and is analyzed as needed.

The reaction temperature can be in a range of 200°–600° C., with a range of 250°–500° C. being preferred. The reaction does not proceed to a substantial extent at temperatures lower than 200° C. Reaction temperatures higher than 600° C. however result in the formation of by-products in larger amounts. Reaction temperatures outside the above range are therefore not preferred.

The reaction pressure may be either an elevated pressure or ambient pressure. An elevated pressure is however preferred from the standpoint of retainability of the catalytic activity. The reaction pressure is preferably in a range of from 200 kPa to 5,000 kPa.

In the present invention, indole or a derivative thereof is obtained from aniline or a corresponding derivative of aniline. Indole or the derivative thereof is called the "indole" herein. The indole can be easily isolated in a pure form from the reaction mixture by a suitable method, for example, by a method known per se in the art such as distillation.

To substantiate the advantages of the invention, the following procedure is followed.

A prepared catalyst is first packed in a reactor. After aniline or a derivative thereof and a polyhydric alcohol are subjected for many hours to the reaction at a predetermined temperature (first run), the catalyst thus used is regenerated.

Using the catalyst thus regenerated, the reaction is conducted likewise for many hours (second run).

In each of these reactions, the reaction mixture is subjected to tap sampling and is analyzed so that the conversion of the reactants and the selectivity to the target compound are determined.

Regeneration of the catalyst is usually carried out in the following manner. The reaction system is purged with N$_2$. After the temperature of the reactor tube is raised to 300° C., N$_2$ gas containing 1.8 vol. % of oxygen is caused to flow at about 90 l/hr so that carbon deposited on the catalyst is burned. The temperature of the reactor tube is raised further to 490° C., at which temperature any carbon still remaining on the catalyst is caused to burn up until the carbon deposit is no longer detected as carbon dioxide and/or carbon monoxide by gas chromatography.

The present invention will hereinafter be described by the following examples. It should however be borne in mind that the invention is not limited to or by the following examples.

EXAMPLE 1

From water glass and zinc nitrate as raw materials, a SiO$_2$—ZnO carrier having a specific surface area of 240 m$^2$/g was prepared by the coprecipitation method. The SiO$_2$—ZnO carrier was immersed for 24 hours in an impregnating solution which had been prepared by adding an excess amount of aqueous ammonia to a 1 wt. % aqueous solution of cobalt nitrate. The thus-immersed carrier is then dried, whereby a carrier containing Co in a proportion of 0.1 on a basis of the atomic ratio to the amount of silver supported was prepared.

The carrier was immersed in an impregnating solution, which has been prepared by dissolving silver acetate in concentrated aqueous ammonia, and in a 4% aqueous hydrazine solution, alternately. The thus-immersed carrier was washed with water and then dried. This procedure was repeated until the amount of silver supported on the carrier reached a predetermined amount, i.e., 10 wt. %, so that a supported silver catalyst with 10 wt. % of silver was prepared.

The catalyst (300 ml) was packed in a reaction tube made of stainless steel and having an inner diameter of 20 mm and then heated to 375° C. under a $N_2$ gas stream.

The $N_2$ was switched to $H_2$, and the catalyst was reduced for 1 hour. The flow rate of $H_2$ was maintained at 90 l/hr and the pressure in the system was controlled at 1.0 MPa by means of regulator valves.

A liquid feed consisting of aniline and ethylene glycol at a molar ratio of 1:0.15 was fed at a flow rate of 200 g/hr by a fixed displacement pump to an evaporator arranged upstream of the reactor tube. At the same time, water was supplied at a flow rate of 106 g/hr to the evaporator.

The resulting gaseous reaction mixture was allowed to flow through a condenser and a gas/liquid separator, whereby non-condensable gas was separated from condensable gas. The non-condensable gas was thereafter released into the atmosphere. Upon elapsed times of 100 hours, 600 hours and 1,200 hours, the condensate was sampled out from the gas/liquid separator which also served as a reservoir for the condensate, and the conversion of ethylene glycol and the selectivity to the target indole were analyzed.

The reaction temperature was gradually raised to 390° C., at which the reaction was conducted for 1,200 hours.

After the 1,200 hour reaction, regeneration of the catalyst was conducted in the following manner. The interior of the reaction system was purged with $N_2$ and the reactor tube was heated to 300° C. $N_2$ gas containing 1.8 vol. % of oxygen was then caused to flow at about 90 l/hr through the reactor tube, whereby carbonaceous substances deposited on the catalyst were burned. This procedure was repeated by raising the temperature of the reactor tube to 490° C.

After the regeneration of the catalyst, the reaction in the second run was conducted in a similar manner to the first run.

Differences in reaction results between the first run and the second run are shown in Table 1.

EXAMPLE 2

A catalyst was prepared in a similar manner to Example 1 except that magnesium nitrate was used as a carrier in place of zinc nitrate and the atomic ratio of Co to silver was changed from 0.1 to 0.2. Using the catalyst thus prepared, the reaction, regeneration and reaction of Example 1 were repeated likewise.

The results are shown in Table 1.

EXAMPLE 3

A catalyst was prepared in a similar manner to Example 1 except that cadmium nitrate was used as a carrier in lieu of zinc nitrate. Using the catalyst thus prepared, the reaction, regeneration and reaction of Example 1 were repeated likewise.

The results are shown in Table 1.

EXAMPLE 4

A catalyst was prepared in a similar manner to Example 1 except that Co was replaced by Ni and the atomic ratio of Ni to silver was changed to 0.08 from the Co/Ag atomic ratio of 0.1. Using the catalyst thus prepared, the reaction, regeneration and reaction of Example 1 were repeated likewise.

The results are shown in Table 1.

EXAMPLE 5

A catalyst was prepared in a similar manner to Example 1 except that magnesium nitrate was used as a carrier instead of zinc nitrate and Co was replaced by Fe. Using the catalyst thus prepared, the reaction, regeneration and reaction of Example 1 were repeated likewise.

The results are shown in Table 1.

COMPARATIVE EXAMPLE 1

The procedures of Example 1 were repeated in exactly the same manner except that the procedure for incorporating Co was omitted upon preparation of the catalyst. The results shown in Table 2 were obtained.

This comparative example corresponds to a conventional technique. It has been clearly demonstrated that, compared with the catalysts of the invention examples, the catalyst of this comparative example underwent more severe deterioration and activity reduction when employed in the reaction for many hours.

COMPARATIVE EXAMPLE 2

The procedures of Example 1 were repeated in exactly the same manner except that the atomic ratio of Co to silver was changed to 0.005 upon preparation of the catalyst. The results shown in Table 2 were obtained.

This comparative example gave results indicative of the lower limit of the effective amount of the additional component to be incorporated in the silver catalyst.

COMPARATIVE EXAMPLE 3

The procedures of Example 1 were repeated in exactly the same manner except that the atomic ratio of Co to silver was changed to 0.3 upon preparation of the catalyst. The results shown in Table 2 were obtained.

This comparative example gave results indicative of the upper limit of the effective amount of the additional component to be incorporated in the silver catalyst.

COMPARATIVE EXAMPLE 4

The procedures of Example 2 were repeated in exactly the same manner except that the atomic ratio of Co to silver was changed to 0.005 upon preparation of the catalyst. The results shown in Table 2 were obtained.

This comparative example gave results indicative of the lower limit of the effective amount of the additional component to be incorporated in the silver catalyst.

COMPARATIVE EXAMPLE 5

The procedures of Examples 2 or 5 were repeated in exactly the same manner except that the procedure for incorporating Co or Fe was omitted upon preparation of the catalyst. The results shown in Table 2 were obtained.

This comparative example corresponds to another conventional technique. It has been clearly demonstrated that, compared with the catalysts of the invention examples, the catalyst of this comparative example underwent more severe deterioration and activity reduction when employed in the reaction for many hours.

COMPARATIVE EXAMPLE 6

The procedures of Example 3 were repeated in exactly the same manner except that the procedure for incorporating Co or Fe was omitted upon preparation of the catalyst. The results shown in Table 2 were obtained.

This comparative example corresponds to a further conventional technique. It has been clearly demonstrated that, compared with the catalysts of the invention examples, the catalyst of this comparative example underwent more severe deterioration and activity reduction when employed in the reaction for many hours.

COMPARATIVE EXAMPLES 7-9

The procedures of Examples 1-5 were repeated in exactly the same manner except that elements other than Co, Fe and Ni were incorporated respectively upon preparation of the catalysts. The results shown in Table 2 were obtained.

These comparative examples correspond to still further conventional techniques in each of which an element other than Co, Fe or Ni is incorporated. It has been clearly demonstrated that, compared with the catalysts of the invention examples, the catalysts of these comparative examples underwent more severe deterioration and activity reduction despite the incorporation of the elements other than Co, Fe and Ni when employed in the reaction for many hours.

It is envisaged that both the examples and the comparative examples gave substantially the same conversion of ethylene glycol and substantially the same selectivity to the target compound when the continuously reacted time was short (not longer than 100 hours).

This is however not the case when the continuously reacted time was long. In the reaction of the first run, the conversion of ethylene glycol (indicated by "C" in the table) by the 1,200 hour reaction in Comparative Example 1 dropped to about 67% of the corresponding conversion achieved in Example 1. In the reaction of the second run, it dropped further to 61%. Activity reduction of a similar degree is observed in the other comparative examples. From these, it is clear that the addition of Co, Fe or Ni is effective in suppressing the reduction of catalytic activity. The addition of Co, Fe or Ni has also been found effective for the activation of catalysts by regeneration.

TABLE 1

| Ex. No. | Carrier | Additional element (content, atomic ratio to Ag) | Number of reaction run(s) | Reaction results (C: EG conversion, S: Indole selectivity) | | |
|---|---|---|---|---|---|---|
| | | | | 100 hr | 600 hr | 1,200 hr |
| 1 | SiO₂—ZnO | Co (0.1) | 1 | C: 100%  S: 78% | C: 96%  S: 74% | C: 88%  S: 71% |
| | | | 2 | C: 100%  S: 78% | C: 95%  S: 75% | C: 85%  S: 70% |
| 2 | SiO₂—MgO | Co (0.2) | 1 | C: 100%  S: 75% | C: 96%  S: 74% | C: 90%  S: 70% |
| | | | 2 | C: 100%  S: 76% | C: 96%  S: 73% | C: 89%  S: 70% |
| 3 | SiO₂—CdO | Co (0.1) | 1 | C: 100%  S: 74% | C: 95%  S: 72% | C: 89%  S: 70% |
| | | | 2 | C: 100%  S: 75% | C: 95%  S: 73% | C: 84%  S: 70% |
| 4 | SiO₂—ZnO | Ni (0.08) | 1 | C: 100%  S: 72% | C: 94%  S: 71% | C: 85%  S: 70% |
| | | | 2 | C: 100%  S: 72% | C: 92%  S: 72% | C: 84%  S: 70% |
| 5 | SiO₂—MgO | Fe (0.1) | 1 | C: 100%  S: 73% | C: 95%  S: 72% | C: 89%  S: 72% |
| | | | 2 | C: 100%  S: 74% | C: 95%  S: 73% | C: 87%  S: 71% |

EG: Ethylene glycol.
Number of reaction run(s): Each run consisted of the reaction for continuous 1,200 hours.

TABLE 2

| Comp. Ex. No. | Carrier | Additional element (content, atomic ratio to Ag) | Number of reaction run(s) | Reaction results (C: EG conversion, S: Indole selectivity) | | |
|---|---|---|---|---|---|---|
| | | | | 100 hr | 600 hr | 1,200 hr |
| 1 | SiO₂—ZnO | None | 1 | C: 100%  S: 78% | C: 82%  S: 70% | C: 59%  S: 65% |
| | | | 2 | C: 99%  S: 77% | C: 77%  S: 71% | C: 52%  S: 67% |
| 2 | SiO₂—ZnO | Co (0.005) | 1 | C: 100%  S: 78% | C: 84%  S: 72% | C: 62%  S: 66% |
| | | | 2 | C: 100%  S: 77% | C: 75%  S: 70% | C: 65%  S: 68% |
| 3 | SiO₂—ZnO | Co (0.3) | 1 | C: 100%  S: 68% | C: 95%  S: 67% | C: 86%  S: 64% |
| | | | 2 | C: 99%  S: % | C: 93%  S: % | C: 83%  S: % |
| 4 | SiO₂—MgO | Co (0.005) | 1 | C: 100%  S: 73% | C: 81%  S: 72% | C: 60%  S: 68% |
| | | | 2 | C: 99%  S: 74% | C: 76%  S: 69% | C: 53%  S: 64% |
| 5 | SiO₂—MgO | None | 1 | C: 100%  S: 74% | C: 79%  S: 70% | C: 65%  S: 67% |

TABLE 2-continued

| Comp. Ex. No. | Carrier | Additional element (content, atomic ratio to Ag) | Number of reaction run(s) | Reaction results (C: EG conversion, S: Indole selectivity) 100 hr | 600 hr | 1,200 hr |
|---|---|---|---|---|---|---|
|  |  |  | 2 | C: 98% S: 75% | C: 74% S: 69% | C: 49% S: 62% |
| 6 | SiO$_2$—CdO | None | 1 | C: 99% S: 74% | C: 80% S: 68% | C: 57% S: 60% |
|  |  |  | 2 | C: 98% S: 72% | C: 76% S: 67% | C: 49% S: 61% |
| 7 | SiO$_2$—ZnO | Cs (0.1) | 1 | C: 98% S: 70% | C: 79% S: 62% | C: 55% S: 58% |
|  |  |  | 2 | C: 96% S: 69% | C: 75% S: 62% | C: 51% S: 57% |
| 8 | SiO$_2$—MgO | B (0.1) | 1 | C: 100% S: 69% | C: 80% S: 67% | C: 58% S: 64% |
|  |  |  | 2 | C: 98% S: 68% | C: 75% S: 65% | C: 53% S: 60% |
| 9 | SiO$_2$—ZnO | Y (0.1) | 1 | C: 100% S: 74% | C: 83% S: 69% | C: 61% S: 64% |
|  |  |  | 2 | C: 98% S: 72% | C: 75% S: 67% | C: 51% S: 64% |

We claim:

1. In a process for preparing an indole compound by reacting an aniline compound selected from the group consisting of aniline, o-toluidine, m-toluidine, p-toluidine, o-haloanilines, m-haloanilines, p-haloanilines, o-aminophenol, m-aminophenol, p-aminophenol, o-anisidine, m-anisidine and p-anisidine with an alcohol selected from the group consisting of ethylene glycol, propylene glycol, 1,2-butanediol, 1,2,4-butanetriol, 2,3-butanediol and diethylene glycol in the presence of a catalyst composed of a carrier having a specific surface area of at least 10 m$^2$/g and silver supported on the carrier, the improvement wherein the catalyst further comprises at least one element selected from Co, Fe and Ni, said at least one element being contained in a range of from 0.01 to 0.20 on a basis of the atomic ratio to the silver.

2. The process of claim 1, wherein the catalyst has been prepared by incorporating said at least one element in said carrier, calcining the resultant carrier at 400°–550° C. and then causing the thus-calcined carrier to support silver.

3. The process of claim 1, wherein said carrier is an oxide of at least one element selected from Si, Al, B, Sb, Bi, Sn, Pb, Ga, Ti, Zr, Be, Mg, Y, Zn, Cd and lanthanide elements, or activated carbon.

4. The process of claim 3, wherein said carrier is an SiO$_2$-containing carrier.

5. The process of claim 4, wherein said SiO$_2$-containing carrier is a carrier which contains SiO$_2$—ZnO, SiO$_2$—CdO, SiO$_2$—MgO or SiO$_2$—SrO.

6. The process of claim 1, wherein the reaction is continuously carried out for at least 1,200 hours.

7. The process of claim 1, wherein after the reaction is continuously carried out for at least 1,200 hours, the catalyst is subjected to regeneration and the reaction is then continued further.

8. The process of claim 1, wherein the reaction is conducted by repeating the cycle that after the reaction is continued, the catalyst is subjected to regeneration and the reaction is then continued further.

9. The process of claim 1, wherein the polyhydric alcohol is reacted in a proportion of 0.05–5 moles per mole of the aniline or the derivative thereof.

10. The process of claim 9, wherein the polyhydric alcohol is reacted in a proportion of 0.1–2 moles per mole of the aniline or the derivative thereof.

11. The process of claim 1, wherein the liquid space velocity of a mixture of the aniline compound and the alcohol, to the catalyst is in a range of 0.01–5 l/l-catalyst/hr.

12. The process of claim 1, wherein the reaction temperature is in a range of 200°–600° C.

13. The process of claim 12, wherein the reaction temperature is in a range of 250°–500° C.

* * * * *